(12) United States Patent
Schnetter

(10) Patent No.: US 10,310,523 B2
(45) Date of Patent: Jun. 4, 2019

(54) METHOD FOR OPERATING A TEMPERATURE CONTROL, APPARATUS FOR A MEDICAL EXAMINATION APPARATUS, A TEMPERATURE CONTROL APPARATUS, AND A MEDICAL EXAMINATION APPARATUS

(71) Applicant: Siemens Healthcare GmbH, Erlangen (DE)

(72) Inventor: Volker Schnetter, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 99 days.

(21) Appl. No.: 15/428,192

(22) Filed: Feb. 9, 2017

(65) Prior Publication Data
US 2017/0227973 A1  Aug. 10, 2017

(30) Foreign Application Priority Data
Feb. 9, 2016 (DE) .......... 10 2016 201 908

(51) Int. Cl.
| | |
|---|---|
| *A61B 5/055* | (2006.01) |
| *G01R 33/31* | (2006.01) |
| *G01R 33/36* | (2006.01) |
| *G05D 23/19* | (2006.01) |
| *G01R 33/54* | (2006.01) |

(Continued)

(52) U.S. Cl.
CPC ......... *G05D 23/1917* (2013.01); *A61B 5/055* (2013.01); *G01R 33/31* (2013.01); *G01R 33/36* (2013.01); *G01R 33/546* (2013.01); *G05B 15/02* (2013.01); *A61B 5/02055* (2013.01); *A61B 5/4266* (2013.01); *A61B 2560/0242* (2013.01); *G01R 33/543* (2013.01)

(58) Field of Classification Search
CPC ........ A61B 2560/0242; A61B 5/02055; A61B 5/055; A61B 5/4266; G01R 33/31; G01R 33/36; G01R 33/543; G01R 33/546; G05B 15/02; G05D 23/1917
See application file for complete search history.

(56) References Cited

U.S. PATENT DOCUMENTS 6,297,634 B1 * 10/2001 Aoki .................... G01R 33/383
324/315
6,909,283 B2 * 6/2005 Emeric .................. G01R 33/28
324/300

(Continued)

*Primary Examiner* — Abdelmoniem I Elamin
(74) *Attorney, Agent, or Firm* — Schiff Hardin LLP

(57) ABSTRACT

A method for operating a temperature control apparatus for a medical examination device, in particular a magnetic resonance apparatus, wherein the medical examination device causes a heat input into the body of a patient to be examined during an examination procedure, and wherein the temperature control apparatus has at least one temperature modifier designed for controlling the temperature of the patient, at least one item of heat information that describes the heat balance of the patient is determined, in order to determine a control parameter for controlling at least one ambient parameter that describes the at least one temperature modifier by taking into account at least one ambient condition on the body of the patient, and at least one examination parameter that describes the examination procedure as the input variables of a heat balance model.

16 Claims, 2 Drawing Sheets

(51) Int. Cl.
  *G05B 15/02* (2006.01)
  *A61B 5/0205* (2006.01)
  *A61B 5/00* (2006.01)

(56) References Cited

U.S. PATENT DOCUMENTS

| | | | |
|---|---|---|---|
| 6,992,483 B1 * | 1/2006 | Emeric | G01R 33/28 324/300 |
| 7,015,692 B2 | 3/2006 | Clarke et al. | |
| 7,304,477 B2 * | 12/2007 | Konijn | F16F 15/02 324/318 |
| 2002/0148604 A1 * | 10/2002 | Emeric | G01R 33/28 165/206 |
| 2004/0017195 A1 * | 1/2004 | Kassai | G01R 33/3856 324/315 |
| 2007/0080689 A1 * | 4/2007 | Konijn | F16F 15/02 324/318 |
| 2009/0215384 A1 | 8/2009 | Wohlfarth | |
| 2013/0035921 A1 | 2/2013 | Rodriguez-Ponce et al. | |
| 2014/0103930 A1 | 4/2014 | Wang et al. | |
| 2014/0249401 A1 | 9/2014 | Van Den Brink et al. | |

\* cited by examiner

METHOD FOR OPERATING A TEMPERATURE CONTROL, APPARATUS FOR A MEDICAL EXAMINATION APPARATUS, A TEMPERATURE CONTROL APPARATUS, AND A MEDICAL EXAMINATION APPARATUS

BACKGROUND OF THE INVENTION

Field of the Invention

The invention concerns a method for operating a temperature control apparatus for a medical examination apparatus, in particular magnetic resonance apparatus, wherein the medical examination device causes a heat input into the body of a patient to be examined during an examination procedure, and the temperature control apparatus has at least one temperature modifier designed to change the temperature of the patient. The invention also concerns a temperature control apparatus, a medical examination apparatus embodying such a temperature control apparatus, and a non-transitory, computer-readable data storage medium encoded with programming instructions that cause such a method to be implemented.

Description of the Prior Art

As is known, in some cases an energy input into the body of a patient occurs when an examination is carried out with a medical examination device, and this can lead to an increase in the patient's trunk temperature. If the medical examination device is a magnetic resonance apparatus, voltages are induced due to the magnetic fields generated during an examination procedure, which voltages can generate an electrical flow of current that heats the body of the patient. Magnetic resonance apparatuses are therefore always designed such that this kind of heating is limited. Limiting such heating also is covered by relevant standards (e.g. TEC 60601-2-33).

The generated heat is dissipated from the body of the patient to the patient's surroundings by convection, thermal radiation and by cooling through evaporation due to the transpiration of the patient that occurs. If these heat loss mechanisms are not enough to dissipate the heat output that occurs during the examination procedure, the trunk temperature of the patient increases. Since the patient frequently reacts with discomfort to an increase of this kind. Standards likewise provide that the increase in the trunk temperature should be limited to a maximum of one degree Celsius. However, the trunk temperature is not generally directly accessible to a measurement and cannot be indirectly determined with sufficient accuracy. It is also known to estimate the trunk temperature by taking into account the specific absorption rate during an examination with a magnetic resonance apparatus, for which purpose an examination interval of six minutes is typically considered. To improve heat loss it is also known to reduce the temperature of the surroundings in which the magnetic resonance apparatus is operated and in which the patient is located. This approach, however, frequently leads to the patient being cold.

It is also known to use fans that cool the patient during the examination procedure. DE 10 2008 010 937 A1 discloses a cooling device for air conditioning an examination room of a medical examination device having a temperature detection device, an air conditioning system for generating conditioned air and an air outlet system arranged inside the examination room. A control unit is provided that controls the air conditioning system on the basis of data detected by the temperature detection device.

A ventilation unit for a magnetic resonance system is known from US 2014/0103930 A1, which has a ventilator. Its operating parameters are controlled as a function of a heat signal that describes a change in heat of an examination subject. In particular, the specific absorption rate can be considered in this connection. Methods of this kind do not take into account the heat loss by the patient to the surroundings, however.

A magnetic resonance apparatus with at least one cooling unit having a cooling pad is known from US 2014/0249401 A1, wherein a control unit is designed to control operation of the cooling unit during an examination as a function of a detected or anticipated temperature of an examination subject. It has been found, however, that a surface-measured or estimated temperature of the patient is a poor indicator of the patient's thermal well-being. Skin temperature, for example, reacts only very slowly to a change in the trunk temperature.

SUMMARY OF THE INVENTION

An object of the invention is to improve the thermal comfort of a patient during an examination procedure by a medical examination device, in particular by a magnetic resonance apparatus.

In a method of the type mentioned in the introduction this object is achieved according to the invention, by determining, in a processor, at least one item of heat information that describes the heat balance of the patient, in order to determine a control parameter therefrom for controlling at least one temperature modifier. The processor derives the control parameter from the output of a heat model that is executed in the processor. The model uses at least one ambient parameter that describes ambient conditions on the body of the patient, and at least one examination parameter that describes the examination procedure, as input variables of the heat balance model.

The invention is based on the conclusion that the individual thermal well-being of a patient is achieved if the patient's heat balance is equalized, i.e. the total amount of heat output generated in the body is essentially equal to the heat output lost by the body. In accordance with the invention, a heat balance model is used in order to determine heat information from which the control parameter for the temperature control apparatus is derived. Heat balance models of this kind are basically known from standards (e.g. ISO 7730, ISO 7933, ISO 9920 or ANSI/ASHRAE 55-2004), but have not previously been used for modeling the heat balance of a patient in the course of medical examinations. The temperature control apparatus can have a controller designed to carry out the method.

The at least one ambient parameter that describes the ambient conditions on the body of the patient, and the at least one examination parameter that describes the examination procedure can be detected. At least one ambient parameter can be measured by a sensor arranged in the vicinity of the patient. At least one examination parameter is expediently transmitted by the examination device. The at least one ambient parameter and the at least one examination parameter are used as input variables for the heat balance model, which is implemented in the controller. The at least one item of heat information that describes the heat balance of the patient is determined by taking into account the at least one ambient parameter and the at least one examination parameter. At least one examination parameter in order to determine the production of heat in the body of the patient, and at least one ambient parameter in order to determine the heat loss by the body of the patient, are taken into account within the scope of the heat balance model. The at least one control parameter for controlling the at least one temperature modifier is determined as a function of the at least one item of heat information. In particular, at least one control parameter is determined for each temperature modifier.

It should be noted that the temperature control effect of the temperature modifier itself can have an effect on the ambient conditions, for example if a temperature modifier designed as a fan is used. In this respect, the at least one control parameter itself or a variable derived from the control parameter can be used as the ambient parameter. The heat information or a further item of heat information can indicate the thermal comfort of the patient on an empirically determined scale, in particular using a comparison group, such as a Predicted Mean Vote (PMV) to ISO 7730.

The inventive method enables significantly more precise assessment of the thermal comfort of the patient, since it is not just a parameter that describes the heat production of the patient's body that is taken into account for controlling the temperature modifier, but also an extensive consideration of the patient's heat balance, i.e. consideration of the heat loss by the patient's body as well. Since it is precisely an equalization of the heat balance that has a significant effect on the trunk temperature, the thermal comfort of the patient that is dependent on the trunk temperature—or in other words, the patient's thermal comfort—is significantly improved during an examination procedure.

Fulfillment of a comfort criterion that describes the thermal comfort of the patient is preferably checked within the scope of the inventive method in order to determine the control parameter. The comfort criterion can evaluate the heat information or an additional variable suitable for assessing the thermal well-being of the patient. A check is preferably made using at least part of the comfort criterion as to whether a balance of activities, described by the heat balance model, namely balance of a loss of heat and heat production, due to the heat input of the medical examination device, is equalized. Such equalization can be considered to exist when the balance lies within an equalization interval extending around an exact equalization. In this respect, the heat information can be heat production information and heat loss information, and a clearance can be applied to the heat production information and the heat loss information in order to determine the equalization. Alternatively or additionally, at least part of the comfort criterion can be aimed at stabilizing the trunk temperature of the patient. In addition, part of the comfort criterion can also evaluate at least one body function parameter of the patient, in particular a body temperature measured on or in the patient's body and/or the patient's cardiac frequency, preferably by the rate of perspiration, transpiration behavior and/or the patient's sensitivity to drafts. It is also conceivable for part of the comfort criterion to directly evaluate an ambient parameter or a variable derived therefrom, in particular a vertical air temperature difference and/or radiation symmetry.

In an embodiment, an indication is provided as an output from the processor to an operator of the medical examination apparatus if it is found that the comfort criterion cannot be fulfilled by a change in the control parameter. It will therefore be concluded from the inability to fulfill the comfort criterion that an influencing factor that cannot be changed by the control parameter should be adjusted in order to improve the heat balance of the patient. For example, the indication can cause the operator to adjust the clothing of the patient. The temperature control processor can have a display monitor at which the indication is shown as a visual output. The indication can also be provided in the form of a warning signal, which can be evaluated at an external display device of the medical examination device.

An examination parameter that describes a specific absorption rate of the patient during the examination procedure is advantageously used within the scope of the inventive method. This describes the thermal effect of the medical examination device on the body of the patient particularly effectively. Since the specific absorption rate is monitored during the examination procedure and/or is calculated in advance of the examination procedure anyway (due to legal requirements), the heat production caused by the medical examination devices can be reliably modeled without significant additional effort. Alternatively or additionally, an examination parameter that describes heat production and/or thermal insulation a local RF coil arranged on the patient can be used, when the magnetic resonance apparatus is operated with local RF coils. Since the local RF coil itself can become heated and therefore cause a heat input into the body of the patient, or thermally insulate the body of the patient at least in certain sections and therefore hinder heat loss, the use of an examination parameter of this kind enables even more precise determination of the heat balance of the patient.

An ambient parameter that describes an air temperature and/or humidity and/or an air velocity and/or a radiation temperature inside a patient-receiving device of the examination device can be used within the scope of the inventive method. These ambient parameters essentially affect heat transfer, in particular due to heat conduction, convection and heat radiation, from the body of the patient to his surroundings, i.e. its heat loss. These ambient parameters are preferably measured by a sensor. An ambient parameter that describes thermal insulation of the patient from the patient's surroundings can also be used, and this describes, for example, thermal insulation due to a patient rest belonging to the medical examination device.

In another embodiment of the inventive method, at least one patient parameter that describes the patient is used as an additional input parameter to the thermal model. Thus, at least one patient parameter can describe the metabolic activity of the patient. The metabolic activity can be derived from at least one patient parameter that describes, for example, the age and/or body mass and/or gender of the patient. In addition, at this at least one patient parameters can describe thermal insulation of the patient, such as the patient's clothing, from the patient's surroundings.

In addition, it is preferred in the inventive method for a control parameter characteristic as a function of time to be calculated in advance for a planned examination procedure. The control parameter characteristic includes a number of values of the control parameter. The method can therefore be carried out as early as before the examination procedure, wherein planning data, calculated in advance, with respect to the examination procedure can expediently be used as the examination parameter. This is particularly advantageous when using a magnetic resonance apparatus as the examination device since here the examination procedure, optionally composed of a number of examination sequences, is typically planned completely in advance, and therefore a control parameter characteristic that is adjusted thereto can be determined. It can advantageously be checked even before the beginning of the examination procedure whether the thermal comfort of the patient is adequate during the examination procedure. Termination of the examination procedure because the patient becomes unwell during the procedure, or an interruption to the examination procedure because the clothing of the patient needs to be changed, can therefore be avoided. Specification of the control parameter characteristic, and accordingly of the course as a function of time of the temperature control effect of the temperature control apparatus, ensures particularly efficient temperature control of the patient.

In another embodiment, the thermal comfort of the patient is monitored during the examination procedure using the comfort criterion. A control parameter characteristic that is updated using current input variables can be determined in the event of an updating criterion being satisfied. New input variables can therefore be detected continuously and a new control parameter characteristic can be determined to ensure the thermal comfort of the patient throughout the entire examination procedure even in the case of changing circumstances. A deviation in a measured input variable of the heat production model from a deviation threshold value can be checked as the updating criterion. Alternatively or additionally, the updating criterion cam be that the control parameter characteristic is determined according to a timing grid, in particular regular timing grid.

Within the scope of the inventive method the at least one control parameter can also be determined outside of examination procedures, in advance of an examination procedure and/or following an examination procedure. The thermal comfort therefore can already be improved by the temperature control of the patient if the patient is already located in a patient-receiving device of the medical examination device, but the examination procedure has not yet begun, i.e., is still being planned. If an increase in trunk temperature of the patient was unavoidable during the examination procedure, the control parameter can also be determined after the end of the examination procedure to enable efficient cooling of the patient.

The volume flow of a fan can be specified as a function of the at least one control parameter, and/or the temperature of a temperature modifier designed for thermally conductive contact with the patient can be specified as a function of the at least one control parameter. The temperature modifier is in this case preferably a temperature-controllable cover or pad on which the patient can lie, or which can be placed on the patient, in particular on the patient's extremities or around the patient's trunk.

The invention also encompasses a temperature control apparatus for a medical examination device, in particular magnetic resonance apparatus that causes a heat input into a body of a patient to be examined during an examination procedure. The temperature control apparatus has at least one temperature modifier operable to control the temperature of the patient. The inventive temperature control apparatus has a controller designed to implement the inventive method.

The invention also encompasses a medical examination apparatus, in particular magnetic resonance apparatus having an inventive temperature control apparatus.

The invention also encompasses a non-transitory, computer-readable data storage medium encoded with programming instructions (program code) that, when the storage medium is loaded into a computer, cause any or all of the embodiments of the method according to the invention as described above to be implemented. The storage medium (data carrier) can be a CD or a DVD, for example.

The description relating to the inventive method is also applicable to the inventive temperature control apparatus, the inventive medical examination apparatus, and the inventive storage medium. The advantages mentioned above can be attained as well by the other aspects of the invention.

DESCRIPTION OF THE PREFERRED EMBODIMENTS

Figure 1:
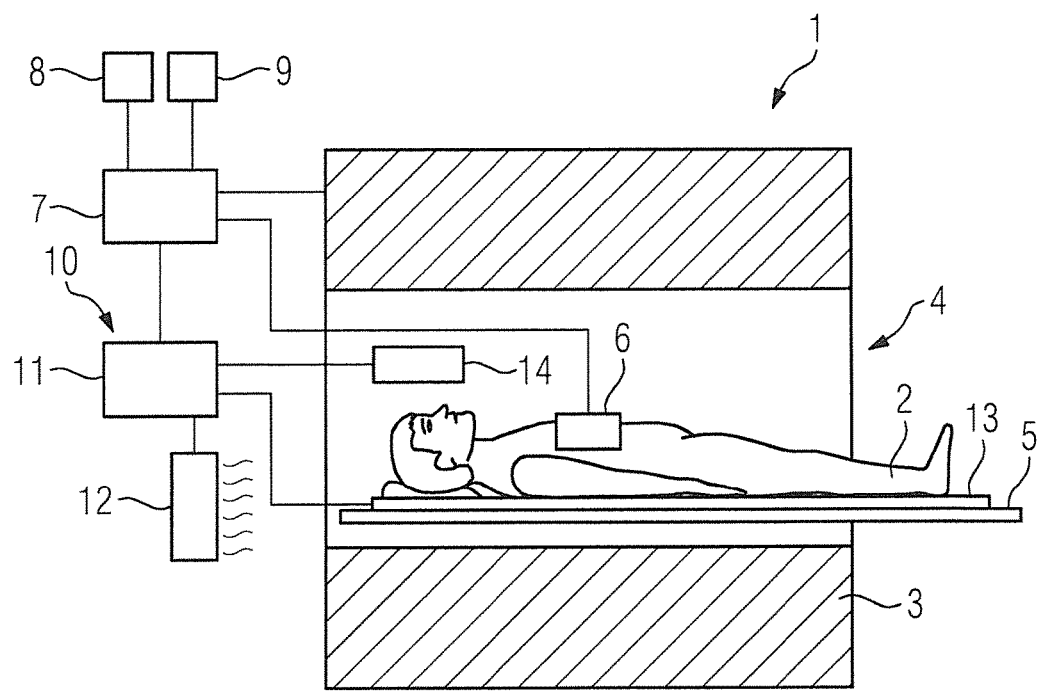
FIG. 1 shows an exemplary embodiment of an inventive medical examination device in which a patient is situated.

FIG. 1 shows an exemplary embodiment of a medical examination device in the form of a magnetic resonance scanner 1 in which a patient 2 is located. The medical examination scanner 1 has a basic field magnet 3, which surrounds a patient-receiving opening 4 having a patient couch 5, a local coil 6 that is arranged on the trunk of the patient 2, a control and evaluation computer 7, an input interface 8 and an output interface 9.

In addition, the medical examination scanner 1 has a temperature control apparatus 10 having a controller 11, and a temperature modifier in the form of a fan 12 directed toward the patient 2, and a pad-like temperature control facilitator 13 can be controlled by the controller 11. The pad-like temperature control facilitator is arranged between the patient 2 and the patient couch 5. In addition, the temperature control apparatus 10 has a sensor 14 (shown schematically), with which any one or more of the air temperature, humidity, air velocity, radiation temperature, vertical air temperature difference and radiation asymmetry inside the patient-receiving device 4 can be measured as ambient parameters, as well as the skin temperature as a body temperature, the cardiac frequency and the rate of perspiration of the patient 2 that describes the transpiration behavior as the patient parameter. The rate of perspiration and the skin temperature are approximated by a first-order low-pass filter. The controller 11 is connected, moreover, to the control and evaluation computer 7 and receives operator entries transmitted from the input interface 8 and send output information to the output interface 9 via the computer 7. In an alternative exemplary embodiment, the temperature control apparatus 10 has its own input interface and its own output interface.

The volume flow generated by the fan 12 can be changed as a function of a control parameter provided by the controller 11. The fan 12 can be put, by a further control parameter into an operating mode that warms the patient 2 and into an operating mode that cools a patient 2. The temperature of the temperature control apparatus 13 can likewise be changed to heat and cool the patient 2 by a control parameter of the controller 11.

Figure 2:
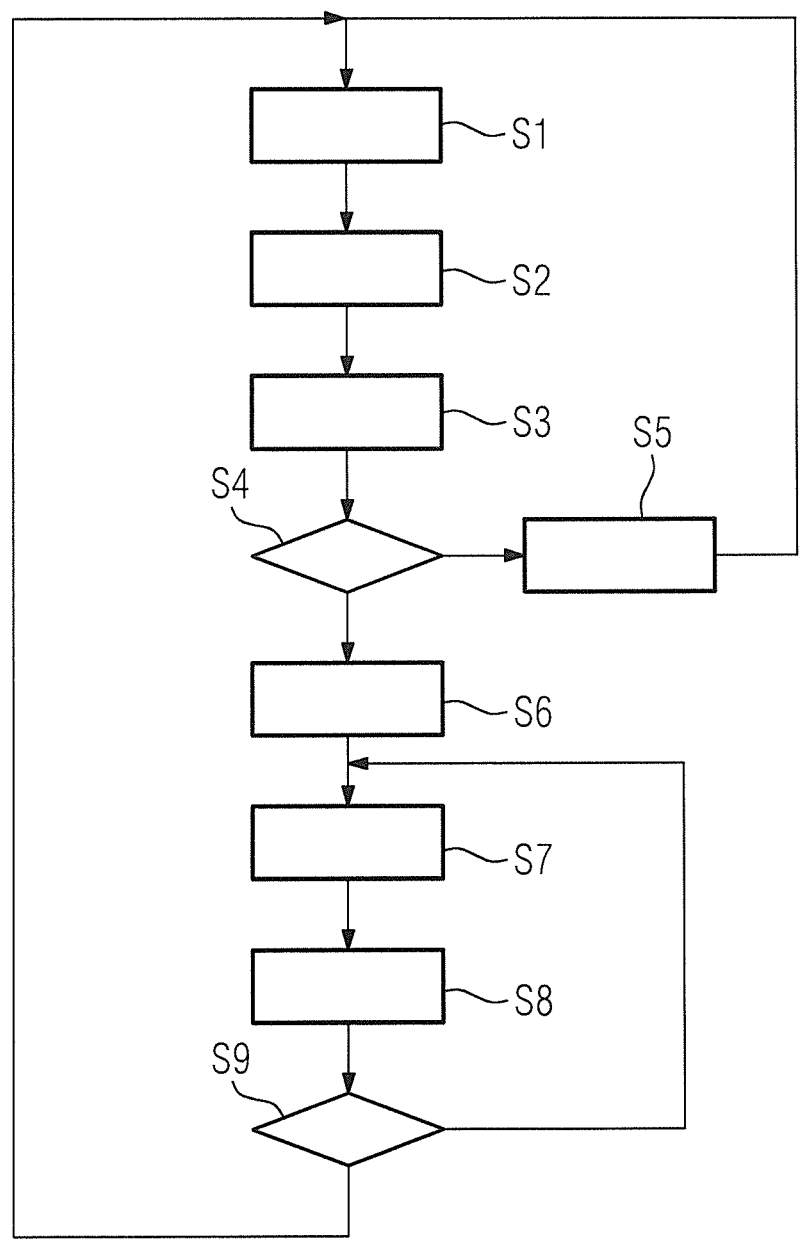
FIG. 2 is shows a flowchart of an exemplary embodiment of the inventive method.

FIG. 2 is a flowchart of an exemplary embodiment of a method for operating the temperature control apparatus 10 for the implementation of which method the controller 11 is designed, and which will be described below:

In a step S1 input variables are detected for a heat balance model that describes the heat balance of the patient 2. For this purpose the controller 11 receives the patient parameters and ambient parameters measured by the sensor 14. In addition, the controller 11 receives examination parameters from the control and evaluation computer 7 in the form of planning data of a planned examination procedure for the patient 2 by the medical examination device 1. These parameters describe a course as a function of time of a specific absorption rate and thermal insulation and heating of the patient 2 by the local coil 6 arranged on his trunk during the examination procedure. The controller 11 receives further patient parameters that describe the age, body mass, gender and clothing of the patient 2 by operating entries by operators of the medical examination scanner 1 in the operating terminal 8.

In a following step S2 an item of heat information that describes the heat balance of the patient 2 is determined by taking into account the examination parameters, ambient parameters and patient parameters.

These parameters are used here as input variables for a heat balance model that models the heat balance of the patient 2. This model describes the heat production inside the body of the patient 2 as a function of the specific absorption rate, heating due to the local coil 6 and a metabolic activity derived from the age, body mass and gender of the patient 2. In addition, the heat balance model describes the heat loss from the body of the patient 2 to his or her surroundings due to heat radiation, convection and heat conduction. For this purpose the model takes into account the ambient parameters and the thermal insulation of the patient 2 by the patient's clothing described by a patient parameter, and the thermal insulation of the patient 2 by the local coil 6 described by an examination parameter. Determination of the heat loss also includes the thermal insulation of the patient 2 by the pad-like temperature control facilitator 13.

The heat information describes the difference in heat production and heat loss by the patient 2 within the content of a balance of activities. Other clearances apart from a difference are also conceivable within the scope of further exemplary embodiments. In addition, a further item of heat information is determined which describes the thermal comfort of the patient 2 on an empirically determined scale, standardized using a comparison group, for which purpose the input variables are also used. The Predicted Mean Vote (PMV) to ISO 7730 is used as the scale.

In a step S3 fulfillment of a comfort criterion that describes the thermal comfort of the patient is checked in order to determine the control parameters. The comfort criterion is aimed at stabilizing the trunk temperature of the patient 2 and checks whether the balance of activities is equalized. This is deemed to be fulfilled if heat production and heat loss lie within a predeterminable equalization interval. The comfort criterion checks, moreover, from body function parameters available to the patient data the measured body temperature, cardiac frequency, transpiration behavior and sensitivity to drafts for adherence to specified limit values. It is likewise checked within the scope of the comfort criterion whether the vertical air temperature difference described as the ambient parameter, and the radiation asymmetry in the patient-receiving device 4 lie within specified limits.

In a step S4 it is checked whether the comfort criterion can be fulfilled by a change in the control parameters for the fan 12 and the temperature control apparatus 13.

If this is not the case, a warning signal is generated in step S5, and this is sent via the control and evaluation computer 7 to the output interface 9 for outputting an indication to the operator of the medical examination device 1. The operator can infer from this indication that, for example, by changing the clothing of the patient 2 or removing or placing a cover from/on the patient 2 they can establish his thermal comfort. The method is then begun again in step S1.

If, by contrast, the result of the check in step S4 is that the comfort criterion can be fulfilled, a control parameter characteristic as a function of time is determined in a step S6 for the fan 12 and the temperature control apparatus 13 in such a way that the comfort criterion is fulfilled.

In a subsequent step S7 the fan 12 and the temperature control apparatus 13 are controlled according to the control parameter characteristic as a function of time.

In a further step S8 variables for checking an updating criterion are detected, and these describe whether re-calculation of a control parameter characteristic as a function of time is necessary. For this purpose the criterion checks the patient parameters for adherence to specified further limit values. Furthermore, the updating criterion provides regular re-determination of the control parameter characteristic using a regular timing grid.

In a step S9 it is checked whether the updating criterion was fulfilled. If this is not the case the method continues in step S7, so the fan 12 and the temperature control apparatus 13 are continuously controlled according to the control parameter characteristic as a function of time, and the updating criterion is checked. If the updating criterion is not fulfilled, by contrast, the method begins again with step S1 to determine an updated control parameter characteristic.

In a further exemplary embodiment of the method, the steps described above and shown in FIG. 2 are carried out first of all before an examination procedure is begun by the medical examination device 1. The thermal comfort of the patient 2 can therefore be ensured as early as during planning of the examination procedure by way of control the fan 12 and the temperature control apparatus 13. First, predefined basic settings can be used for the input variables, in particular with respect to the air temperature, humidity, clothing and a mean specific absorption rate. In this regard, the fact that the thermal load is time-dependent due to the specific absorption rate is taken into account. In particular, the evaluation of the comfort criterion as early as before the beginning of the examination procedure enables a check as to whether thermal comfort is foreseeably given for the entire duration of the examination procedure. Since in the case of the medical examination device designed as a scanner 1, the complete examination procedure, having a number of examination sequences is pre-planned, the control parameter characteristic can also be planned accordingly. An interruption or termination of an ongoing examination procedure can be avoided by outputting the indication.

Once the examination procedure has begun, the method is carried out continuously, so the thermal comfort of the patient is optimally ensured for the entire duration of the examination procedure, in particular even in the case of an unplanned change in circumstances determined by the ambient parameters and patient parameters. The method is also continued after the end of the examination procedure. It can therefore be ensured that in the case of an unavoidable increase in trunk temperature the patient can be efficiently cooled in order to quickly restore thermal comfort.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a temperature control apparatus for a medical examination apparatus, said medical examination apparatus executing an examination procedure on a patient that causes a heat input into the body of the patient, and said temperature control apparatus comprising at least one temperature modifier, said method comprising:

during said examination procedure, providing a processor with an electronic representation of at least one ambient condition on the body of the patient, and at least one examination parameter that describes said examination procedure;

in said processor, using said at least one ambient condition and said at least one examination parameter as inputs to a heat balance model that models whether a state of balance exists between heat production in the body of the patient during said examination procedure, and heat loss by the patient during said examination procedure, from which a heat balance state of the patient is determined as an output of the heat balance model;

from said heat balance state of the patient provided as the output of said heat balance model, determining, in said processor, a value of a control parameter for said temperature modifier that controls at least one ambient parameter that is influenced by said temperature modifier, said value being determined so as to operate said temperature modifier to maintain or restore equality, during said examination procedure, of said heat production and said heat loss; and providing said control parameter, having said value, from said processor to said temperature modifier at a selected time relative to said examination procedure, and thereby operating said temperature modifier with said control parameter at said value.

2. A method as claimed in claim 1 comprising determining said control parameter in said processor by evaluating a comfort criterion, provided to the processor, that describes thermal comfort of the patient dependent on said heat balance state.

3. A method as claimed in claim 2 comprising, in said processor, implementing a check based on said comfort criterion as to whether said heat balance state is equalized so as to be within an equalization interval in a range around an exact equalization.

4. A method as claimed in claim 3 comprising providing an indication from said processor to an operator of said medical examination apparatus if said check indicates that said comfort criterion cannot be fulfilled by a change in said value of said control parameter.

5. A method as claimed in claim 2 comprising using, as said comfort criterion, stabilization of a trunk temperature of the patient.

6. A method as claimed in claim 1 wherein said medical examination apparatus is a magnetic resonance scanner comprising a local radio-frequency (RF) coil, and comprising providing said processor with said examination parameter selected from the group consisting of a specific absorption rate of the patient during said examination procedure, thermal insulation relative to the patient provided by said local RF coil, and heat production by said local RF coil during said examination procedure.

7. A method as claimed in claim 1 comprising providing said processor with said ambient parameter selected from the group consisting of air temperature in said medical examination apparatus, humidity in said medical examination apparatus, air velocity in said medical examination apparatus, and radiation temperature within a patient receiving receptacle of said medical examination apparatus.

8. A method as claimed in claim 1 comprising providing said computer with at least one patient parameter that describes the patient, selected from the group consisting of metabolic activity of the patient and thermal insulation of the patient from an environment associated with said medical examination apparatus, and using at least one patient parameter in said processor as an additional input to said heat balance model.

9. A method as claimed in claim 1 comprising, in said processor, calculating a control parameter characteristic of said control parameter as a function of time in advance of said examination procedure.

10. A method as claimed in claim 9 comprising monitoring thermal comfort of the patient during said examination procedure, and updating said control parameter characteristic, upon occurrence of an updating criterion, using current input variables determined during said monitoring.

11. A method as claimed in claim 1 comprising selecting said at least one control parameter at a time outside of said examination procedure.

12. A method as claimed in claim 1 comprising using a fan as said temperature modifier, said fan having a volume flow that is specified dependent on said value of said at least one control parameter.

13. A method as claimed in claim 1 comprising using a pad that is in thermally conductive contact with the patient as said temperature modifier, said pad having a temperature that is specified dependent on said value of said at least one control parameter.

14. A temperature control apparatus for a medical examination apparatus, said medical examination apparatus executing an examination procedure on a patient that causes a heat input into the body of the patient, said temperature control apparatus comprising:

at least one temperature modifier;

a processor provided, during said examination procedure, with an electronic representation of at least one ambient condition on the body of the patient, and at least one examination parameter that describes said examination procedure;

said processor being configured to use said at least one ambient condition and said at least one examination parameter as inputs to a heat balance model that models whether a state of balance exists between heat production in the body of the patient during, said examination procedure, and heat loss by the patient during said examination procedure, from which a heat balance state of the patient is determined as an output of the heat balance model;

said processor being configured to determine, from said heat balance of the patient provided as the output of said heat balance model, a value of a control parameter for said temperature modifier that controls at least one ambient parameter that is influenced by said temperature modifier, said value being determined so as to operate said temperature modifier to maintain or restore equality, during said examination procedure, of said heat production and said heat loss; and said processor being configured to provide said control parameter, having said value, from said processor to said temperature modifier at a selected time relative to said examination procedure, and thereby operating said temperature modifier with said control parameter at said value.

15. A medical examination apparatus comprising:

a medical examination scanner that executes an examination procedure on a patient that causes a heat input into the body of the patient;

at least one temperature modifier;

a processor provided, during said examination procedure, with an electronic representation of at least one ambient condition on the body of the patient, and at least one examination parameter that describes said examination procedure;

said processor being configured to use said at least one ambient condition and said at least one examination parameter as inputs to a heat balance model that models whether a state of balance exists between heat production in the body of the patient during said examination procedure, and heat loss by the patient during said examination procedure, from which a heat balance of the patient is determined as an output of the heat balance model;

said processor being configured to determine, from said heat balance of the patient provided as the output of said heat balance model, a control parameter for said temperature modifier that controls at least one ambient parameter that is influenced by said temperature modifier, said value being determined so as to operate said temperature modifier to maintain or restore equality, during said examination procedure, of said heat production and said heat loss; and said processor being configured to provide said control parameter, having said value, from said processor to said temperature modifier at a selected time relative to said examination procedure, and thereby operating said temperature modifier with said control parameter at said value.

16. A non-transitory, computer-readable data storage medium encoded with programming instructions, said storage medium being loaded into a computer that operates a temperature control apparatus for a medical examination apparatus, said medical examination apparatus executing an examination procedure on a patient that causes a heat input into the body of the patient, and said temperature control apparatus comprising at least one temperature modifier, said programming instructions causing said computer to:

receive, during said examination procedure, an electronic representation of at least one ambient condition on the body of the patient, and at least one examination parameter that describes said examination procedure;

use said at least one ambient condition and said at least one examination parameter as inputs to a heat balance model that models whether a state of balance exists between heat production in the body of the patient that occurs during said examination procedure, and heat loss by the patient during said examination procedure, from which a heat balance state of the patient is determined as an output of the heat balance model;

from said heat balance of the patient provided as the output of said heat balance model, determine a value of a control parameter for said temperature modifier that controls at least one ambient parameter that is influenced by said temperature modifier, said value being determined so as to operate said temperature modifier to maintain or restore equality, during said examination procedure, of said heat production and said heat loss; and provide said control parameter, having said value, from said computer to said temperature modifier at a selected time relative to said examination procedure, and thereby operate said temperature modifier with said control parameter at said value.

* * * * *